(12) United States Patent
Holmes et al.

(10) Patent No.: US 10,786,342 B2
(45) Date of Patent: Sep. 29, 2020

(54) DOSING APPARATUS

(71) Applicant: Mark L. Anderson, Spring Valley, WI (US)

(72) Inventors: Robert Holmes, Auckland (NZ); Paul Buckley, Auckland (NZ); Malcolm Lynd, Drury (NZ)

(73) Assignee: Imaginus Limited (NZ)

( * ) Notice: Subject to any disclaimer, the term of this patent is extended or adjusted under 35 U.S.C. 154(b) by 178 days.

(21) Appl. No.: 15/987,445

(22) Filed: May 23, 2018

(65) Prior Publication Data

US 2019/0358010 A1  Nov. 28, 2019

(51) Int. Cl.
*A61D 7/00* (2006.01)
*A61M 31/00* (2006.01)

(52) U.S. Cl.
CPC .............. *A61D 7/00* (2013.01); *A61M 31/00* (2013.01); *A61M 2205/19* (2013.01); *A61M 2205/586* (2013.01); *A61M 2210/1007* (2013.01); *A61M 2250/00* (2013.01)

(58) Field of Classification Search
CPC ........... A61D 7/00; A61D 1/02; A61M 31/00; A61M 2210/1007; A61M 2205/19; A61M 2205/586; A61M 2250/00; A61M 5/24; A61M 2005/2403; A61M 2005/2414; A61M 5/3204; A61M 5/3134; A01J 3/00
See application file for complete search history.

(56) References Cited

U.S. PATENT DOCUMENTS

2013/0158475 A1*  6/2013  Xia ..................... A61M 39/1011
                                                              604/94.01
2017/0000594 A1*  1/2017  Buckley ................... A61D 7/00

* cited by examiner

*Primary Examiner* — Amber R Stiles
*Assistant Examiner* — Daniel Moore
(74) *Attorney, Agent, or Firm* — Skinner and Associates; Joel D. Skinner, Jr.

(57) ABSTRACT

A doser including one or more cartridges for holding one or more products. The cartridge has a body defining a cavity for holding the products, a nozzle disposed on the body and connected to the cavity for dispensing the product from the cavity, and a piston arranged to move within the cavity to propel the product from the cavity into the nozzle. The cartridge also has a cap removably coupled to the cartridge for protecting the nozzle. Lastly, the doser has a dispenser for holding the cartridge or cartridges which actuates the piston, and removes the cap from the cartridge, so that the product is dispensed from the cartridge.

13 Claims, 21 Drawing Sheets

DOSING APPARATUS

37 C.F.R. § 1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

BACKGROUND

1. Field

The present invention relates, generally, to agriculture. More particularly, the invention relates to agricultural diseases. Most particularly, the invention relates to a system, apparatus and method for preventing mastitis.

2. Background Information

Mastitis is a significant animal health problem affecting global dairy production. Dosing a herd of dairy cows to treat or protect against mastitis can be a very labor-intensive exercise. For example, the organization Dairy NZ suggests a treatment procedure estimated to take approximately 3 minutes per cow. It is important that scrupulous hygiene is observed to ensure the treatment is successful. But with an average time of 3 minutes, it means that to give blanket dry cow treatment to all cows in the average New Zealand herd of say 400 cows, over 20 hours of time would be expended. This indicates just how time consuming the process can be. The problem can be accentuated in cases where a new dosing syringe has to be obtained and manipulated for each cow.

A further issue with treating cows for mastitis is that the equipment used should be scrupulously clean. It should not itself present a source of bacterial contamination. However, with many known dosing syringes it is necessary to remove a cover cap by hand each time a cow is dosed. This presents an opportunity for bacterial infection to pass to the syringe, and therefore to the cows.

It is an object of a preferred embodiment of the present invention to provide a dosing apparatus which goes at least some way towards overcoming one or more of the above For these and other reasons, a need exists for the present invention.

All US patents and patent applications, and all other published documents mentioned anywhere in this application are hereby incorporated by reference in their entirety.

BRIEF SUMMARY

The present invention provides a dosing apparatus and method which is practical, reliable, accurate and efficient, and which is believed to fulfill a need and to constitute an improvement over the background technology.

In one aspect, the invention provides a dosing apparatus, comprising:

(a) at least one cartridge for holding at least one product, the cartridge having a body defining a cavity for holding the at least one product, a nozzle disposed on the body and communicatively connected to the cavity for dispensing the at least one product from the cavity, and a piston arranged to move within the cavity to propel the at least one product from the cavity into the nozzle;

(b) a cap removably coupled to the cartridge for protecting the nozzle; and (c) a dispenser for holding the at least one cartridge, and adapted to actuate the piston, and remove the cap from the cartridge, whereby the at least one product is dispensed from the at least one cartridge.

In another aspect, the invention provides a dosing apparatus for administering a prophylactic or therapeutic mastitis product to the teat of a dairy cow, comprising:

(a) at least one cartridge for holding at least one product, the cartridge having:
(i) a body defining a cavity for holding the at least one product,
(ii) a nozzle disposed on the body and communicatively connected to the cavity for dispensing the at least one product from the cavity, the nozzle being disposed at an angle, relative to the body of approximately 60 degree, and
(iii) a piston arranged to move within the cavity to propel the at least one product from the cavity into the nozzle;

(b) a cap removably coupled to the cartridge for protecting the nozzle, and wherein the cap comprises a shoulder portion and a cover portion, the shoulder portion removably engaging the exterior of the body, the cover portion extending away from the shoulder portion and covering the nozzle, and wherein the shoulder portion has a pair of wings; and (c) a dispenser for holding the at least one cartridge, and adapted to actuate the piston, and remove the cap from the cartridge, whereby the at least one product is dispensed from the at least one cartridge, the dispenser comprising, and wherein the plunger type mechanism comprises a 78, and 80, 66, a 76, and a 70.

The aspects, features, advantages, benefits and objects of the invention will become clear to those skilled in the art by reference to the following description, claims and drawings.

BRIEF DESCRIPTION OF THE SEVERAL VIEWS OF THE DRAWING

The present invention, and the manner and process of making and using it, will be better understood by those skilled in the art by reference to the following drawings.

DETAILED DESCRIPTION

A. The System

Figure 1:
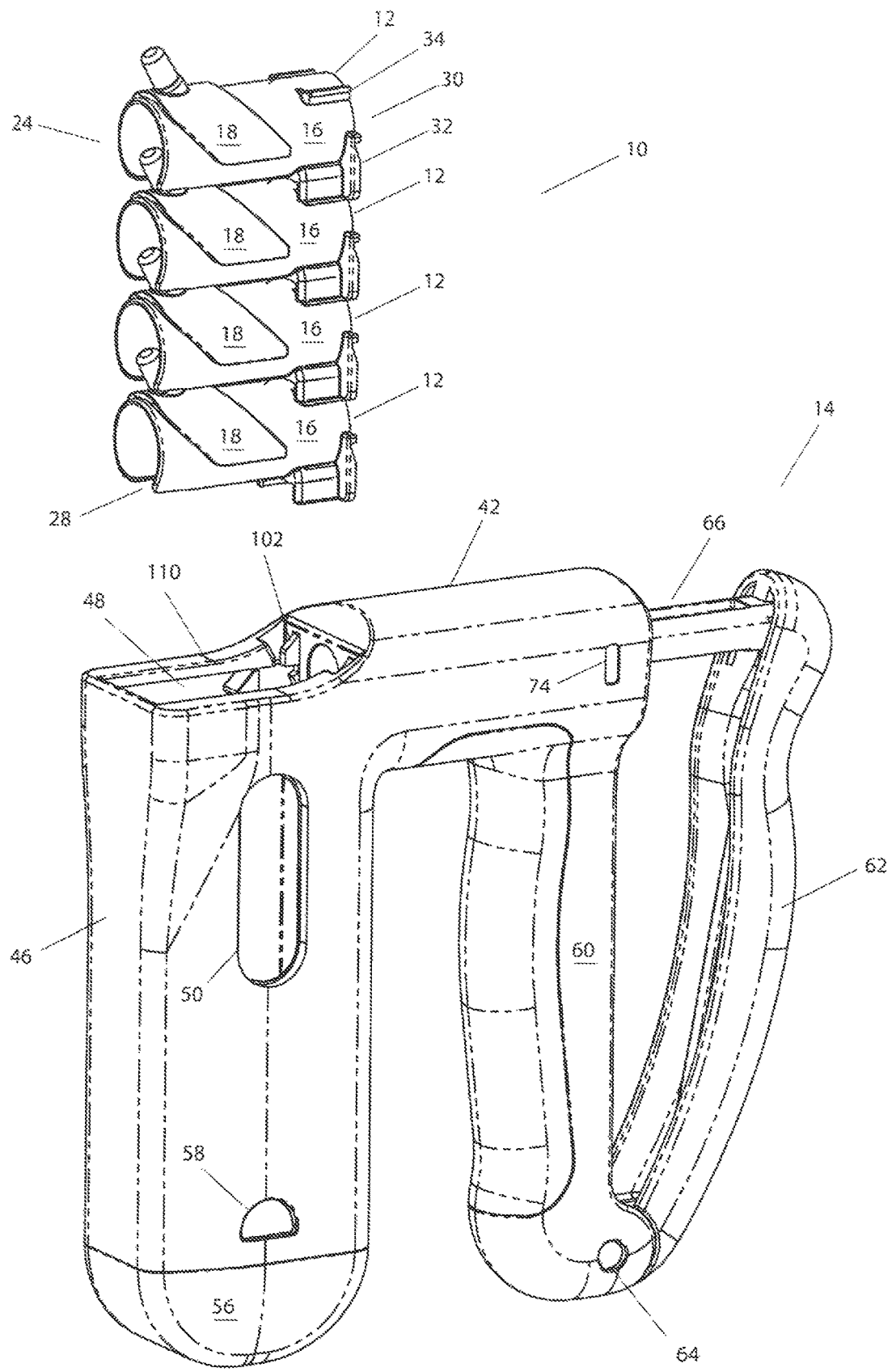
FIG. 1 is a perspective view of an embodiment of the system of the invention, comprising a dispenser gun into which a stack of cartridges is inserted.
Figure 2:
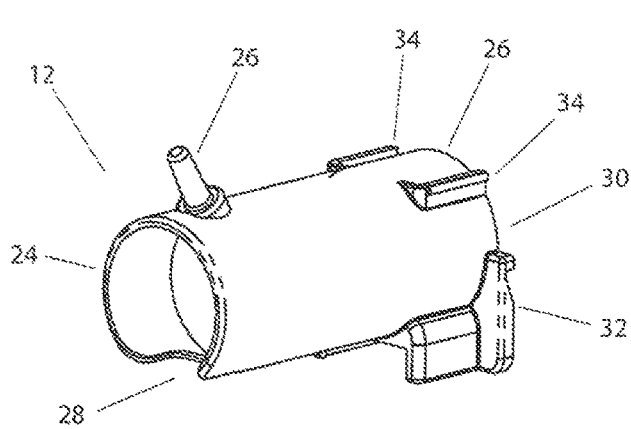
FIG. 2 is a front perspective view of an embodiment of an individual cartridge.
Figure 7:
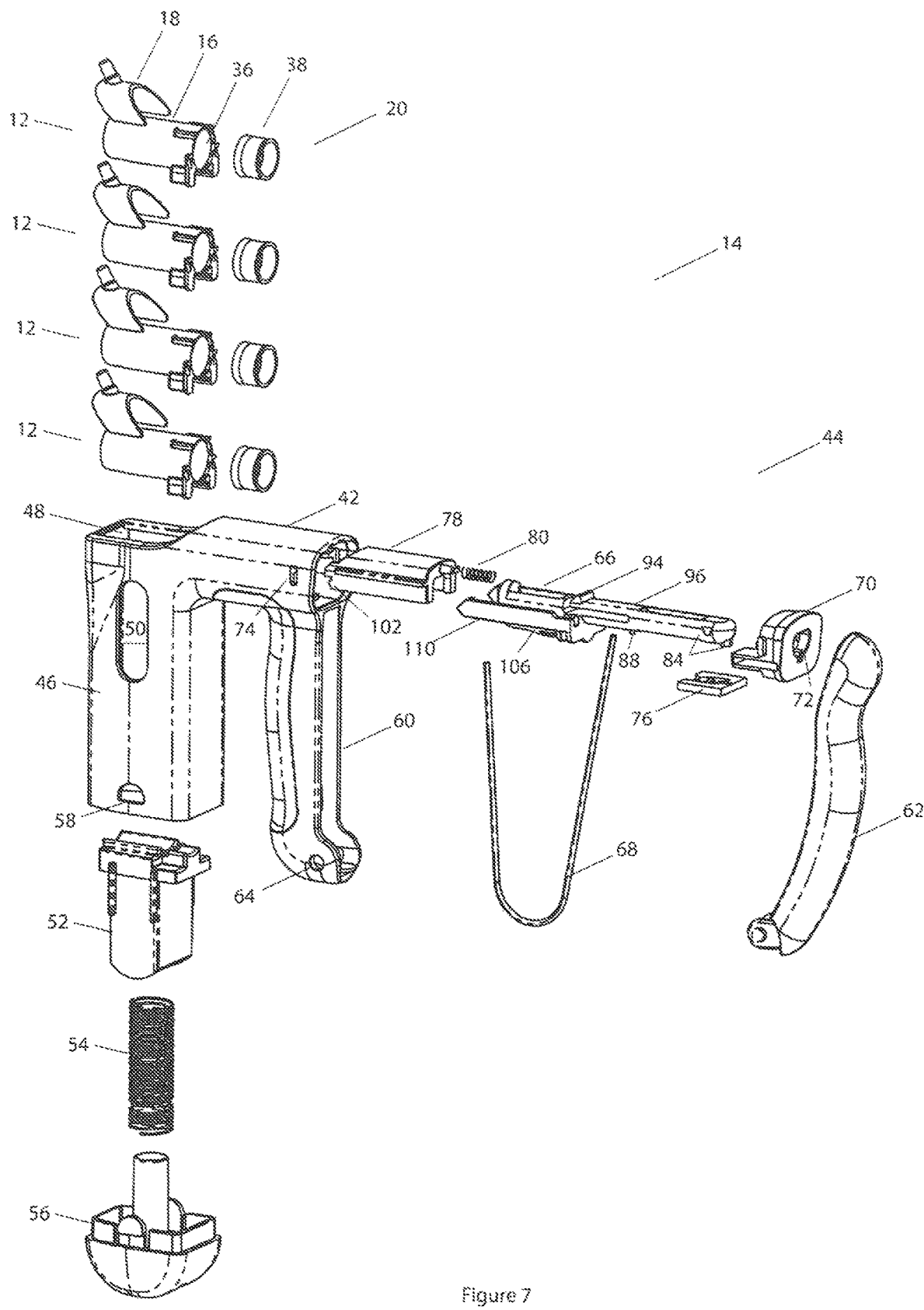
FIG. 7 is an exploded view of an embodiment of the system of the invention.
Figure 8:
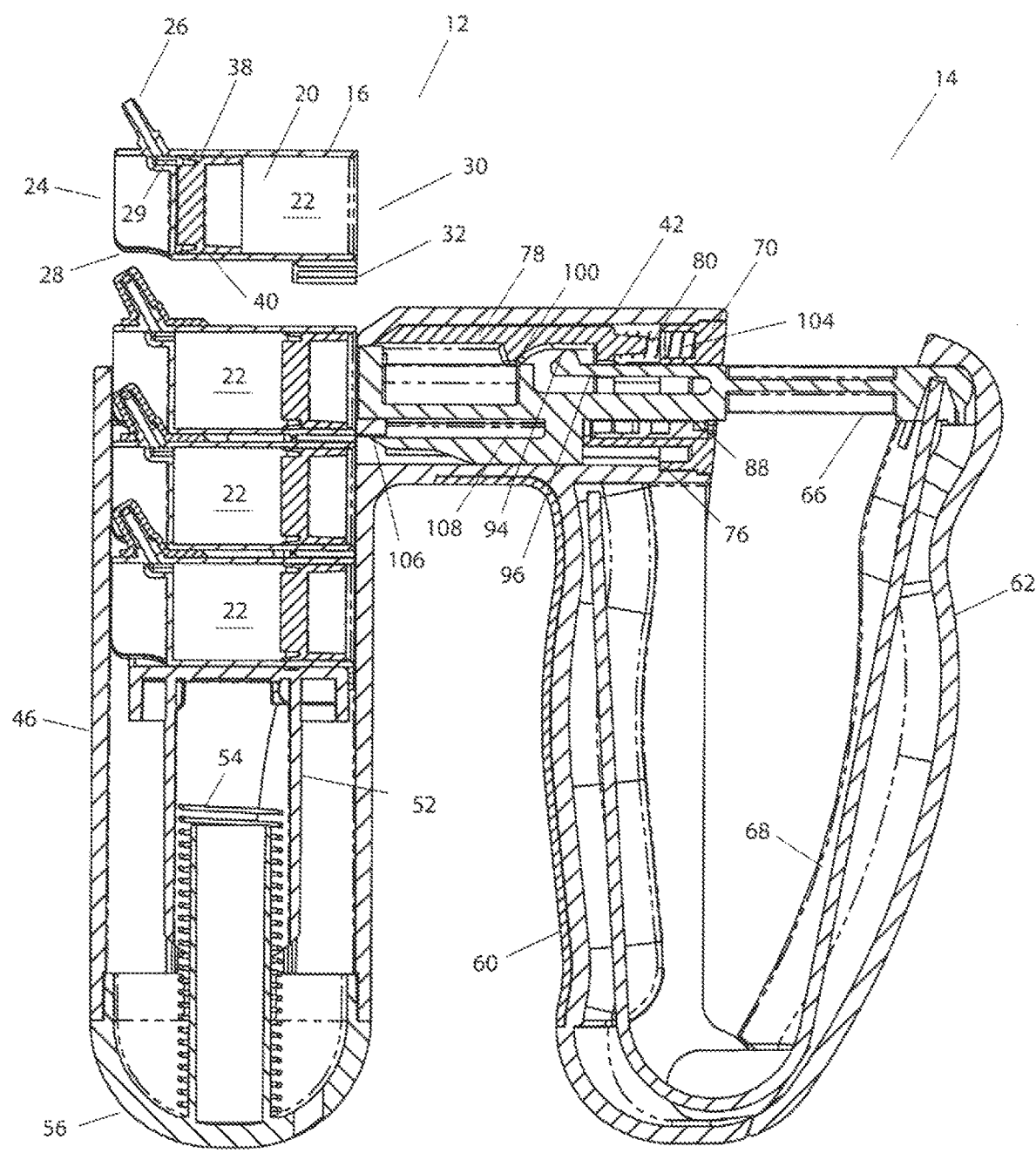
FIG. 8 is a cross-sectional view of the dispenser gun.
Figure 9:
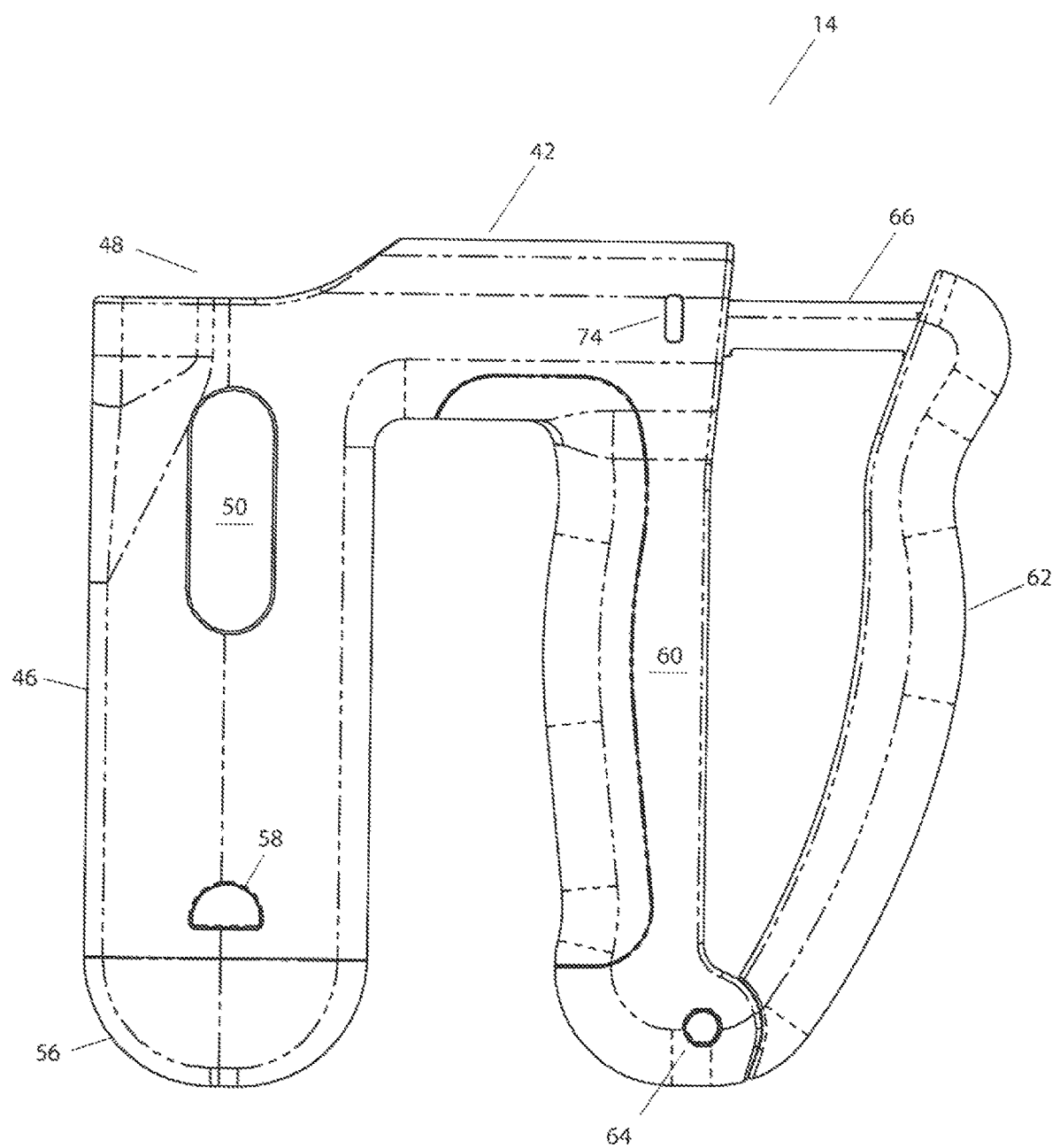
FIG. 9 is a side elevation view of an embodiment of the dispenser gun of the invention.
Figure 10:
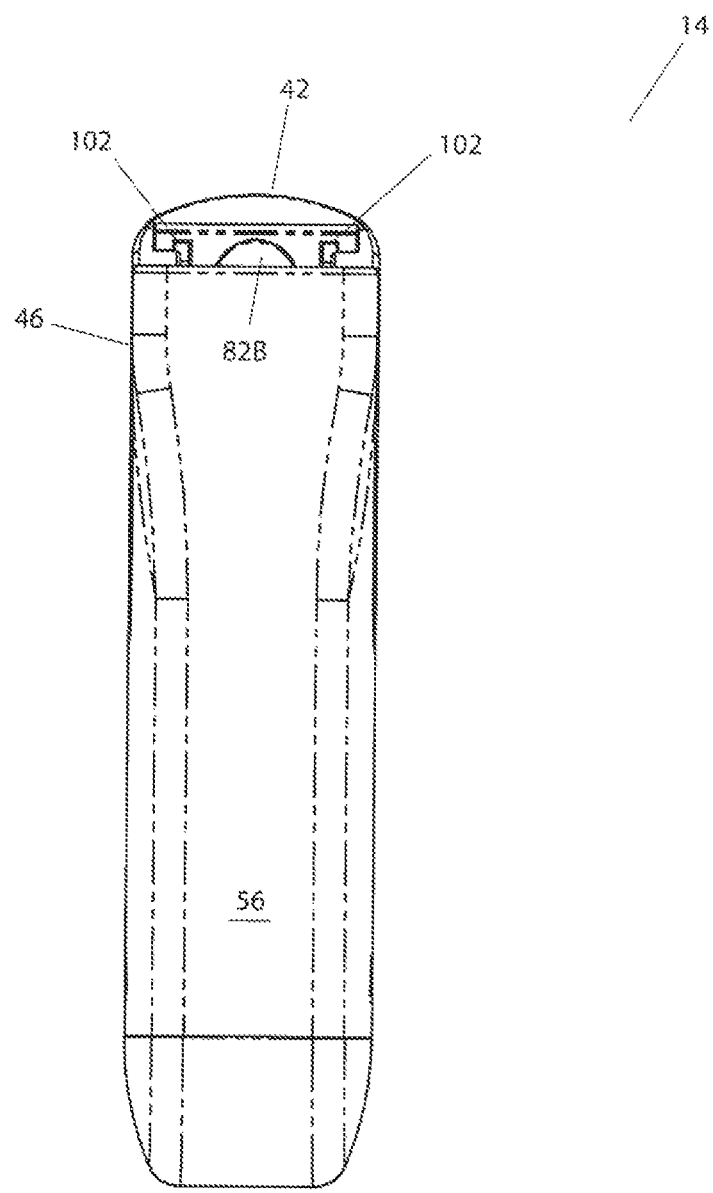
FIG. 10 is a front end view of the dispenser gun.
Figure 11:
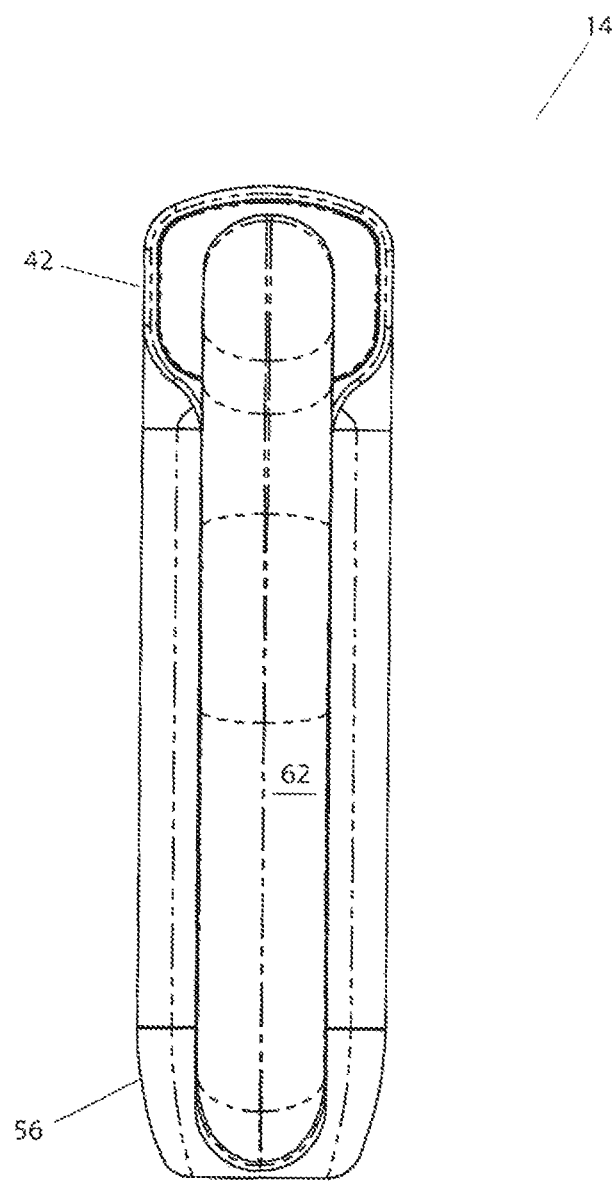
FIG. 11 is a rear end view of the dispenser gun.
Figure 12:
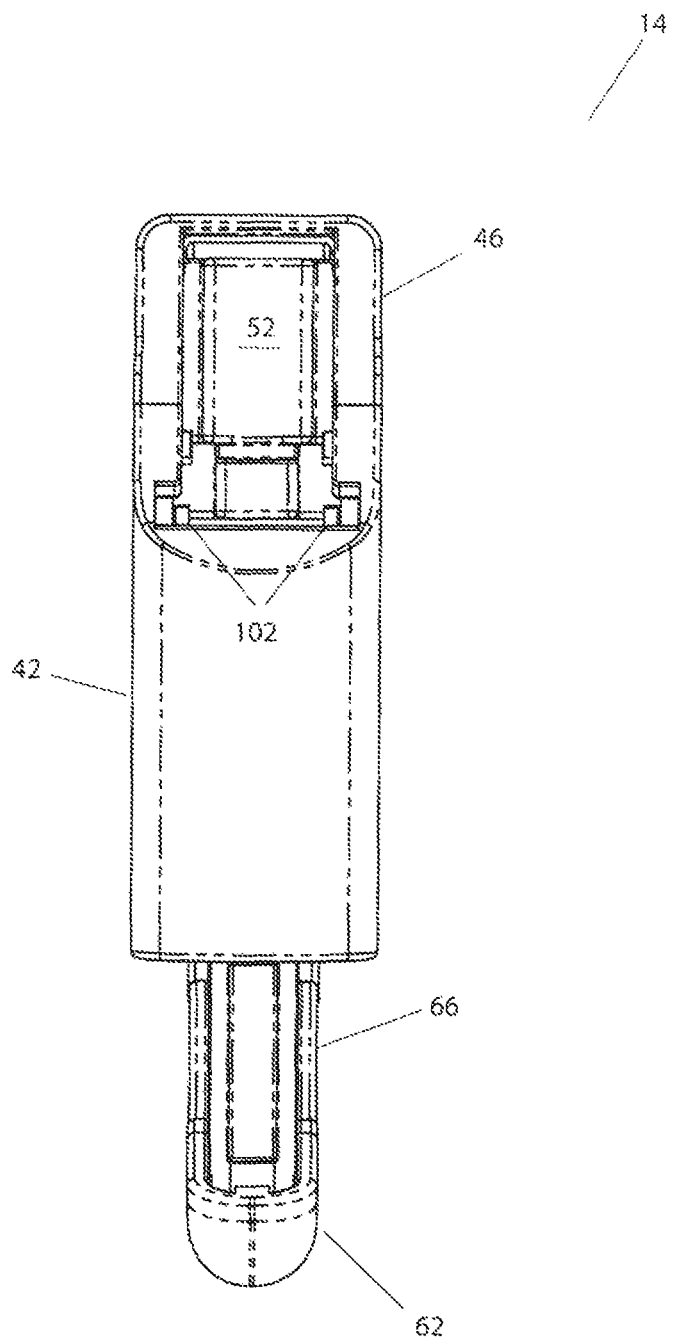
FIG. 12 is a top plan view of the dispenser gun.
Figure 13:
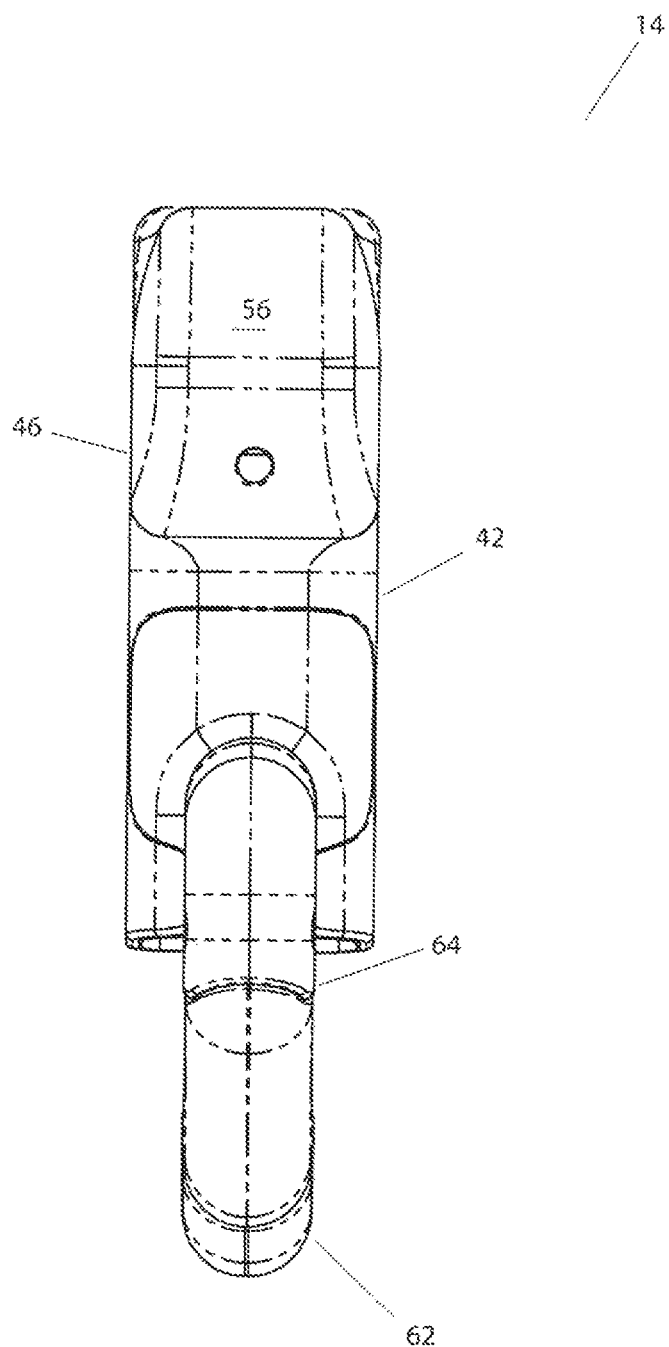
FIG. 13 is a bottom plan view of the dispenser gun.
Figure 14:
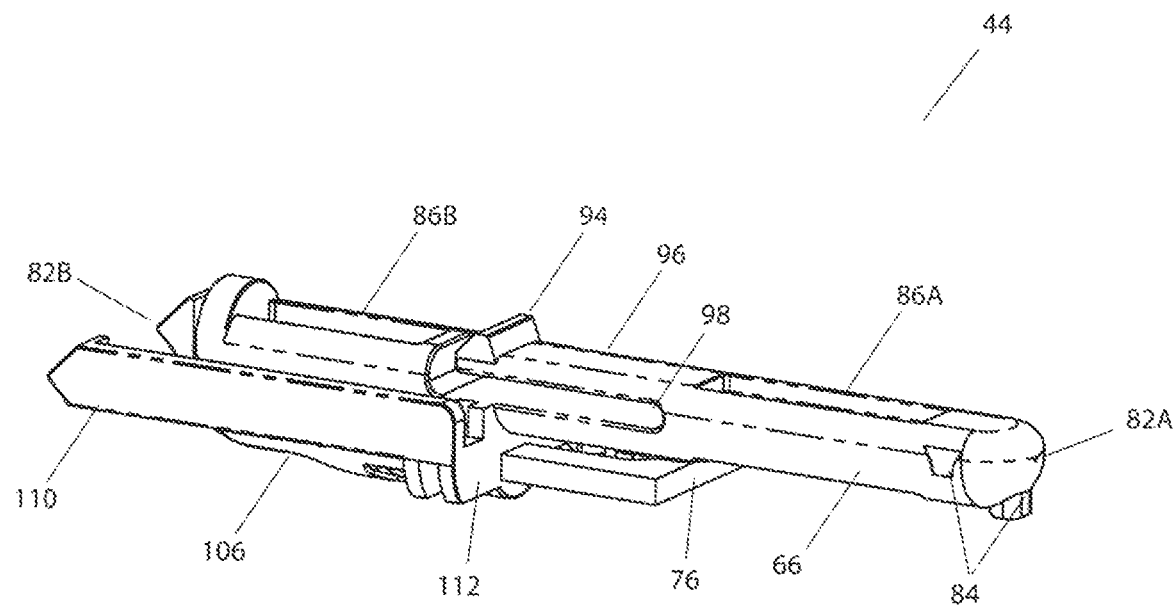
FIG. 14 is a perspective view of an embodiment of a plunger assembly of the dispenser gun.
Figure 15:
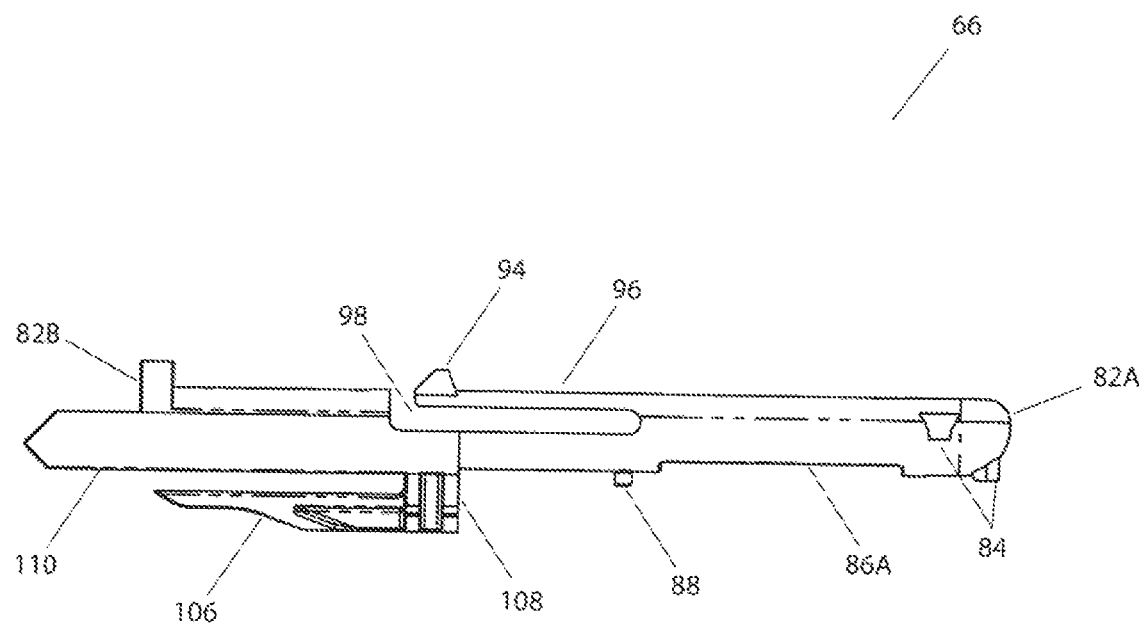
FIG. 15 is a side elevation view of the plunger assembly.
Figure 16:
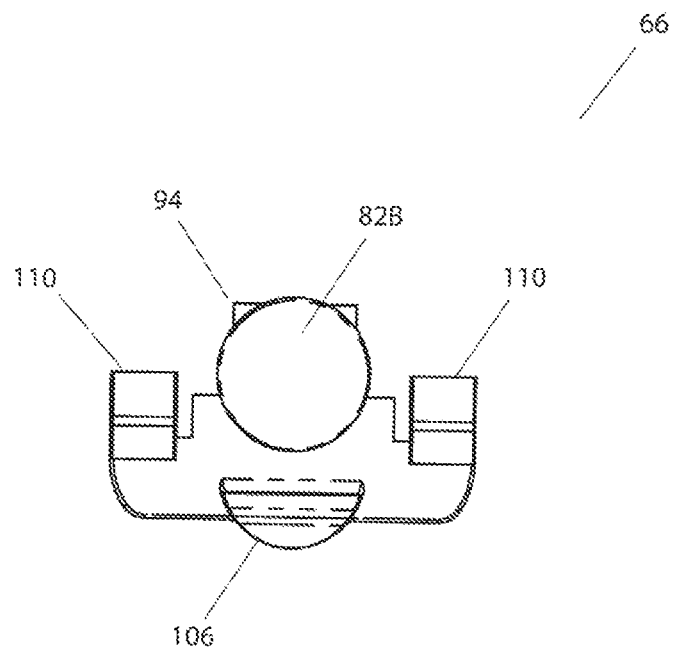
FIG. 16 is a front end view of the plunger assembly.
Figure 17:
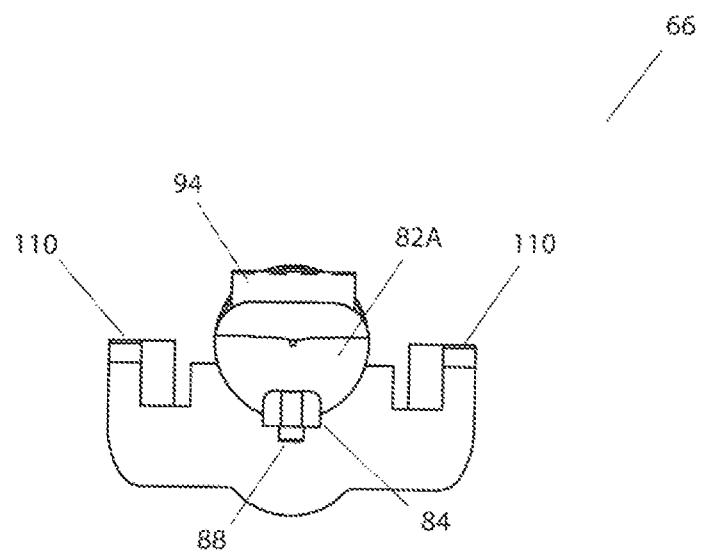
FIG. 17 is a rear end view of the plunger assembly.

A preferred embodiment of the system 10 of the invention is shown in FIGS. 1, 7 and 8. A cartridge 12 is used with a dispenser 14, and is primarily intended for dosing small quantities of antibiotic paste or teat sealant product into the teat canals of the udders of dairy cows or similar milk producing animals. As best shown in FIG. 7, each cartridge 12 is composed of three separate parts: a body 16, a cap 18, and a piston 20.

B. The Cartridge

Referring also to FIGS. 2-6, the cartridge body 16 has a cavity 22 for holding a product to be dosed. A distal, forward end 24 of the body 16 has a nozzle 26, which is preferably in the form of a cannula, on the top, dorsal surface, and an indentation 28 on the bottom, ventral surface, which receives the nozzle 26 of the underlying cartridge 12. In the embodiment shown, the nozzle 26 protrudes approximately 7 mm at an angle from the body 16 of approximately 60 degrees. The nozzle 26 is communicatively connected to the cavity 22 via a short passage 29, and is configured for channeling the product within the cavity 22 into an orifice of an animal. At a proximal, rearward end 30 of the body 16 it features a pair of hooks 32, and a pair of complementary tabs 34. These two pairs are configured to facilitate interlocking between adjacent cartridges 12, and the vertically straight sides of the pair of hooks 32 help to keep the cartridges 12 aligned when situated within the dispenser gun 14.

Figure 3:
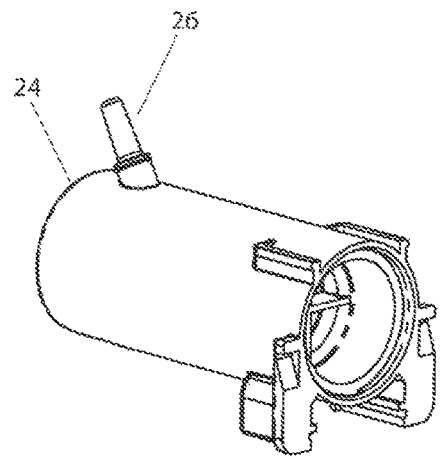
FIG. 3 is a rear perspective view of the cartridge.

The cap 18 fits over the nozzle 26, and has a curvilinear design which wraps tightly around the cylindrical body 16. It also reaches laterally along the body 16 toward the proximal, rearward end 30, terminating at rounded tips on either side of the body 16. The cylindrically shaped piston 20, as viewed through a proximal aperture 36 in FIG. 3, is flush with the wall of the cavity 22. The piston 20 has a cup seal 38 about the periphery of its distal end, facing the product within the cavity 22. For this reason, as the piston 20 is pushed further into the cylindrically shaped cavity 22, the pressure within the product acts to push the outer lips of the cup seal 38 outwards to help maintain a seal between the piston 20 and the inner wall of the cavity 22. In this embodiment, the piston 20 also has piston skirts 40 which keep it aligned with the cylindrically shaped cavity 22.

Figure 4:
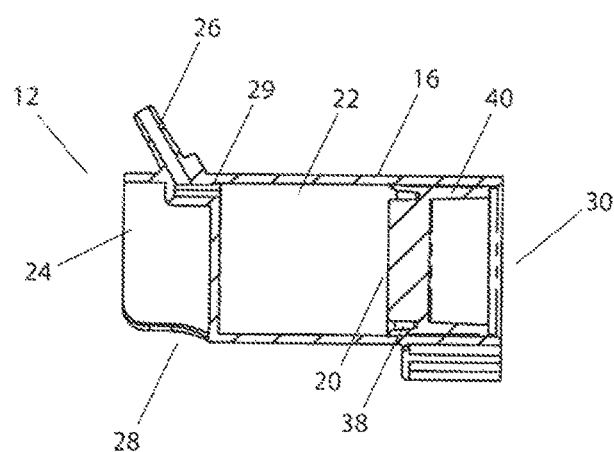
FIG. 4 is a cross-sectional view of the cartridge.
Figure 5:
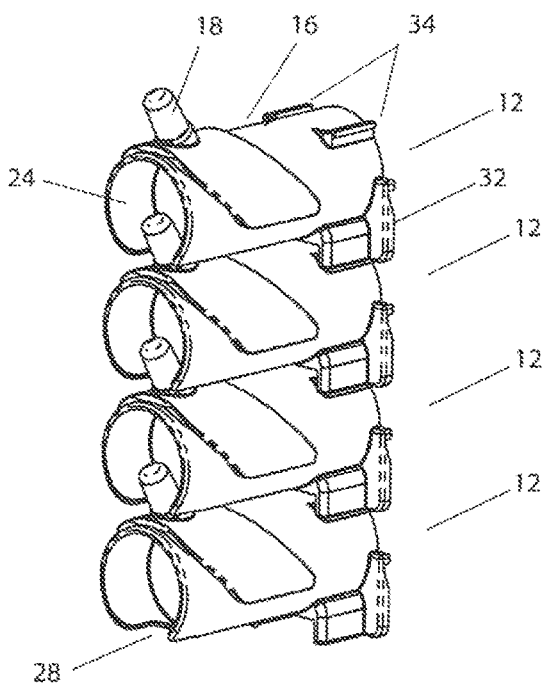
FIG. 5 is a perspective view of a stack of cartridges, with each cartridge's nozzle fitting into the recess in the cartridge above it, and all cartridges fitted with a nozzle cap.
Figure 6:
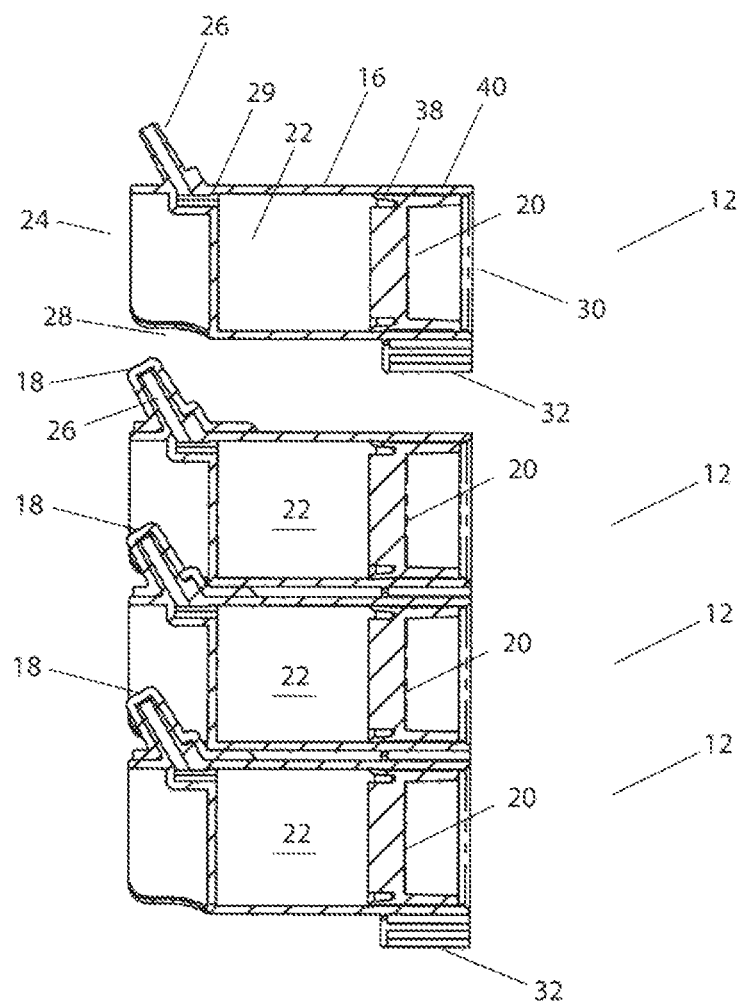
FIG. 6 is a cross-sectional view of the stack of cartridges, with the top cartridge separated.

As best shown in FIG. 4, a helpful feature of the cartridge 12 is that the longitudinal axis of the nozzle 26 is at an angle to the longitudinal axis of the body 16 of the cartridge 12. Ideally, the longitudinal axis of the nozzle 26 is at an angle of between forty-five and ninety degrees to the longitudinal axis of the body 16, and in this embodiment the axis of the nozzle 26 is at an angle of about sixty degrees to the axis of the body 16. This angled configuration of the nozzle 26 allows the user of the dispenser gun 14 and cartridges 12 to apply the dose of the product vertically upwards and into the teat canals without unduly twisting his or her hands to orient the nozzle 26 to suit the orientation of the teats.

C. The Dispenser Gun

Referring again to FIGS. 1, 7 and 8, the dispenser gun 14 generally consists of actuator or main body 42 which provides structure and a means of operating the invention by hand, and a plunger assembly 44 for engaging with the cartridges 12 one by one and advancing the pistons 20 of the cartridges 12 to dispense product held within the cavity 22 of each cartridge 12. FIGS. 8-13 show further details of the body 42 of the dispenser gun 14.

The front column of the body 42 of the gun 14 serves as a magazine 46, which stores the dosing cartridges 12 and feeds them upward into a breach 48 one after the other. On the side of the magazine 46 is a vertically disposed viewing aperture 50 which allows the user to visually determine the number of cartridges 12 remaining in the magazine 46. Inside the magazine 46, the stack of cartridges 12 is cradled from the bottom by a follower 52, which itself is urged upwards by a magazine spring 54. The magazine spring 54 uses a magazine cap 56 as a support/foundation, while the cap 56 is configured to clip in through a pair of clip apertures 58 on both sides of the magazine 46, thus securing the magazine cap 56 to the magazine 46 and sealing the open-ended bottom of the front column of the body 42 from dirt and debris.

The rear column of the body 42 forms a handle 60, by which the user holds and operates the dispenser gun 14. The handle 60 supports a lever-style trigger mechanism 62, pivoting from and attaching by clip-in at a pair of handle apertures 64. The handle 60 and trigger 62 are ergonomically shaped with comfortable gripping surfaces. The trigger mechanism 62 is configured to push a plunger body 66 when pushed forward as the hand of the user squeezes the trigger 62 and handle 60 together. A trigger spring 68 returns the trigger 62 and the plunger 66, which is connected to the trigger 62, to a withdrawn position when a hand squeeze action is released. A handle cap 70 with an aperture 72 allows the plunger 66 to slide in and out of the body 42 in a stabilized manner. The handle cap 70 is configured to clip into a pair of body apertures 74 on either side of the body 42, thus sealing the section of the body 42 enclosing the plunger assembly 44 from the rear.

The plunger assembly 44 of the dispenser gun 14 consists of four separate parts, as best shown in FIG. 7: the plunger body 66, a grooved block 76, a slide 78, and a slide spring 80. Referring also to FIGS. 14-19, a proximal rearward end 82A of the plunger body 66 features an attachment means in the form of a hook and pair of indentations 84 for mating with complementary structures inside the top end of the trigger mechanism 62. This pivotal attachment enables the trigger 62 to push and pull the plunger body 66 when squeezed by the user and returned by the trigger spring 68, respectively. Near the rearward end 82A is a large hollow section 86A disposed vertically within the plunger body 66, with a similar hollow section 86B disposed vertically near a distal forward end 8213 of the plunger body 66. This enables the plunger body 66 to flex laterally as a cylindrically shaped knob 88, about 2 mm in length, on its ventral surface is guided through the grooved block 76 positioned directly under said knob 88 within the body 42 of the dispenser gun 14.

Figure 20:
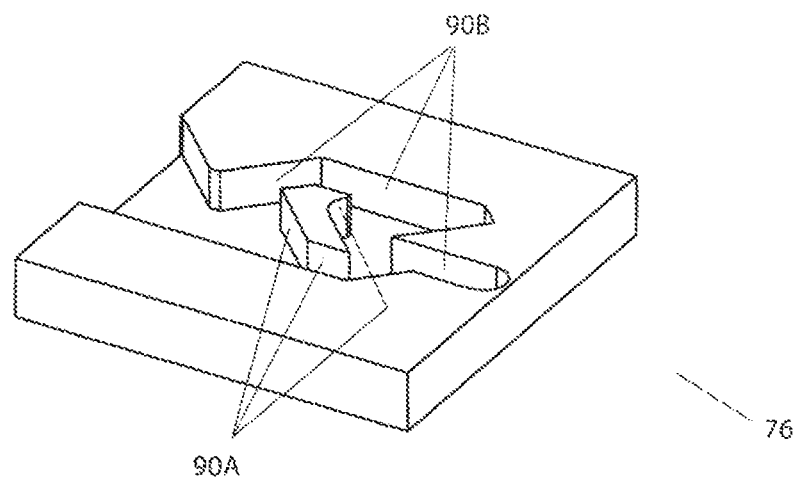
FIG. 20 is a perspective view of an embodiment of the grooved block.
Figure 21:
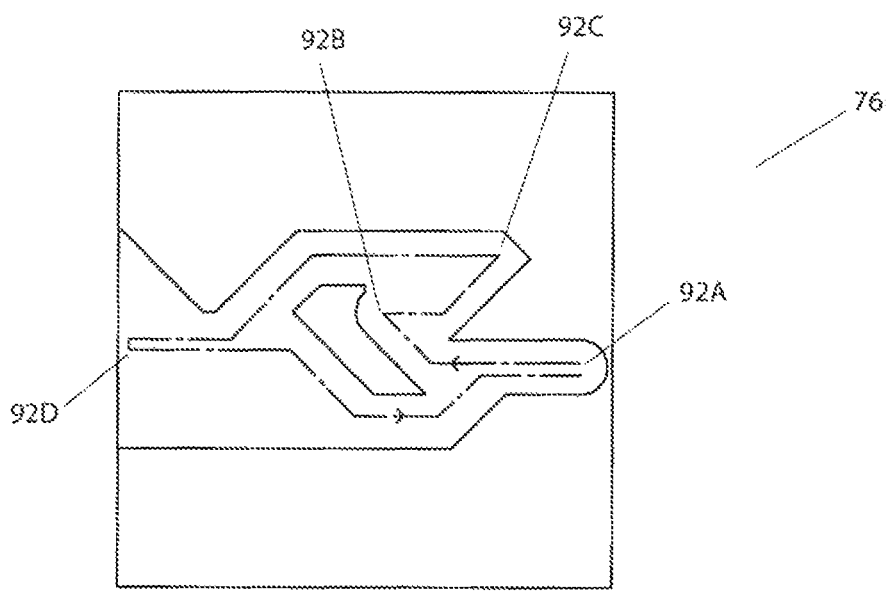
FIG. 21 is a top plan view of the grooved block.

Referring also to FIGS. 20 and 21, The grooved block is square shaped, having a thickness of approximately 3 mm, with an inner groove carved out to form an inner and outer wall 90 A&B which guide the knob 88 through a succession of positions 92 A-D. The function of the grooved block 76 is to divide the actuation sequence into a first hand-squeeze action for cap 18 removal and a second hand-squeeze action for expelling the product. Referring specifically to FIG. 21, the knob 88 begins in position 92A. As the plunger 66 is initially advanced, the knob 88 encounters the inner wall 90A and is guided to position 92B. Following an initial release of the trigger 62 as the cap 18 of the cartridge 12 is removed, the plunger body 66 moves backward momentarily and the knob 88 is guided by the outer wall 90B to position 92C. The trigger 62 is then engaged a second time, and as the plunger 66 advances, the outer wall 90B guides the knob 88 to position 92D. At this point the plunger body 66 has reached its limit of extension, thus the knob 88 remains in position 92D until the trigger 62 is released again. The inner wall 90A then guides the knob 88 back to position 92A to complete the cycle.

Referring to FIGS. 7, 8, 14 and 15, the plunger body 66 includes a plunger barb 94 situated on a flexible arm 96 which extends horizontally over a groove 98 in the medial dorsal surface of the plunger body 66. The plunger barb 94 is configured to catch on a corresponding slide barb 100 on the ventral surface of the slide 78 when the plunger body 66 is moving back to its initial retracted state.

Figure 22:
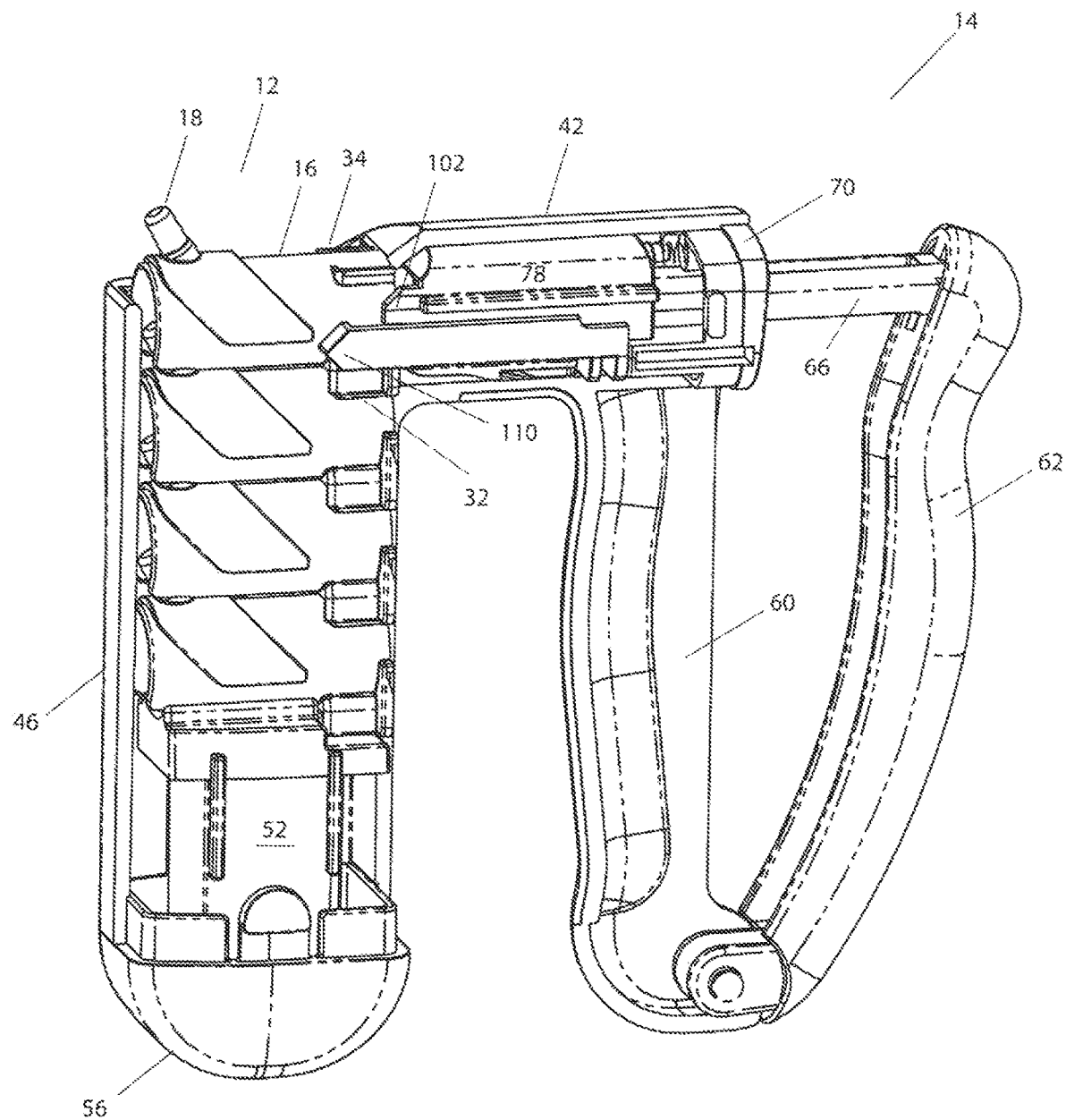
FIG. 22 is a front perspective view of the dispenser gun, cut away to show a plunger assembly and the stack of cartridges loaded into a magazine of the gun, in an initial state.

As depicted in FIG. 22, protruding from the front end of the slide 78 are a pair of slide tabs 102, which extend into the upward path of the cartridge 12, and catch on the flat upper surfaces of the hooks 32, therefore providing a cartridge 12 retaining means. In its extended position the slide 78 retains the cartridge 12 within the breach 48, and the cartridge 12 is stabilized against the slide tabs 102 by the upward force of the magazine spring 54. When the plunger barb 94 catches on the slide barb 100, the plunger body 66 momentarily retracts the slide 78 and allows the spent cartridge 12 to be ejected. Referring again to FIG. 8, along with the plunger body 66, the slide 78 is withdrawn until it contacts a recess 104 in the handle cap 70, forcing the plunger barb 94 under as it continues withdrawing with the plunger body 66. The slide 78 is then forcefully reextended by the slide spring 80 in order to retain the next cartridge 12 in the stack.

The plunger body 66 also includes a means of separating adjacent cartridges 12 from one another in the form of a wedge-shaped blade 106. The blade 106 runs parallel to the plunger body 66 and is physically connected to it by a short vertical arm 108. When the plunger body 66 is advanced to push product from the cartridge 12 situated within the breach 48, the blade 106 advances at the same time. The blade 106 is aligned with the space between the cartridge 12 in the breach 48 and the cartridge 12 immediately below it. As the blade 106 advances, the wedge shape of the blade 106 causes the two cartridges 12 to separate. This allows the upper cartridge 12 to be ejected immediately after the slide 78 is withdrawn.

Figure 18:
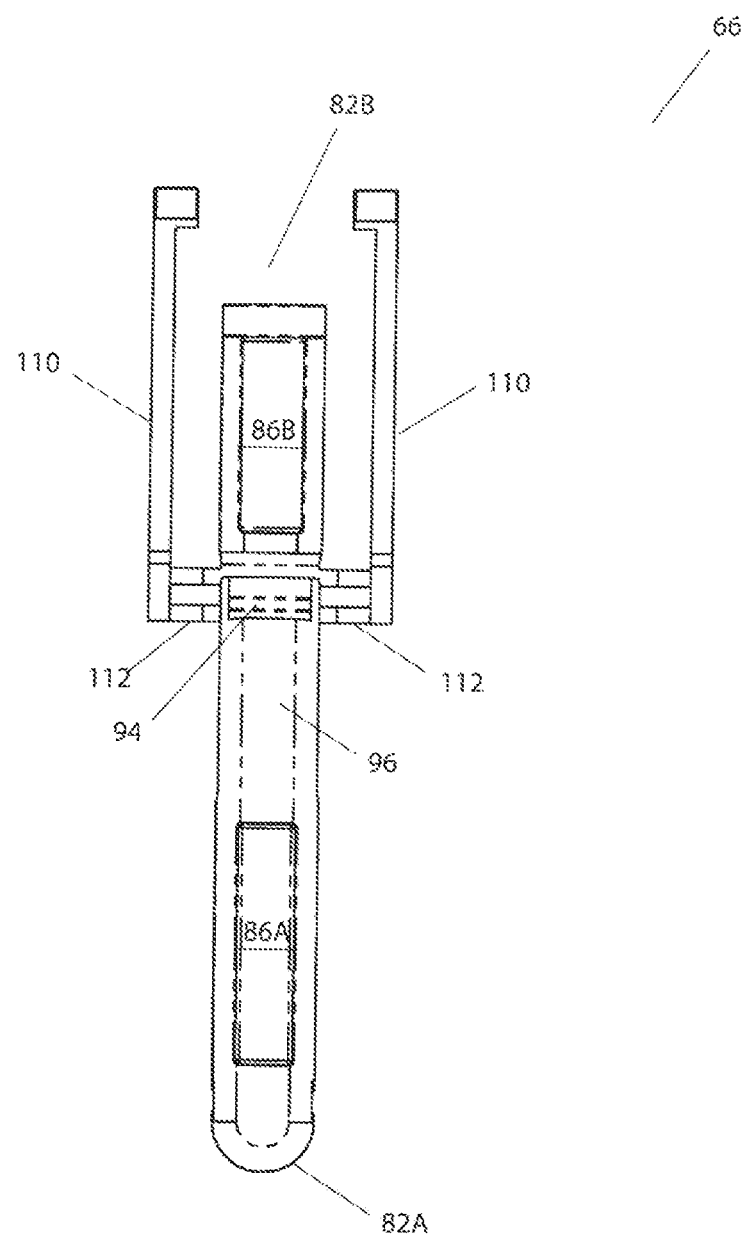
FIG. 18 is a top plan view of the plunger assembly.
Figure 19:
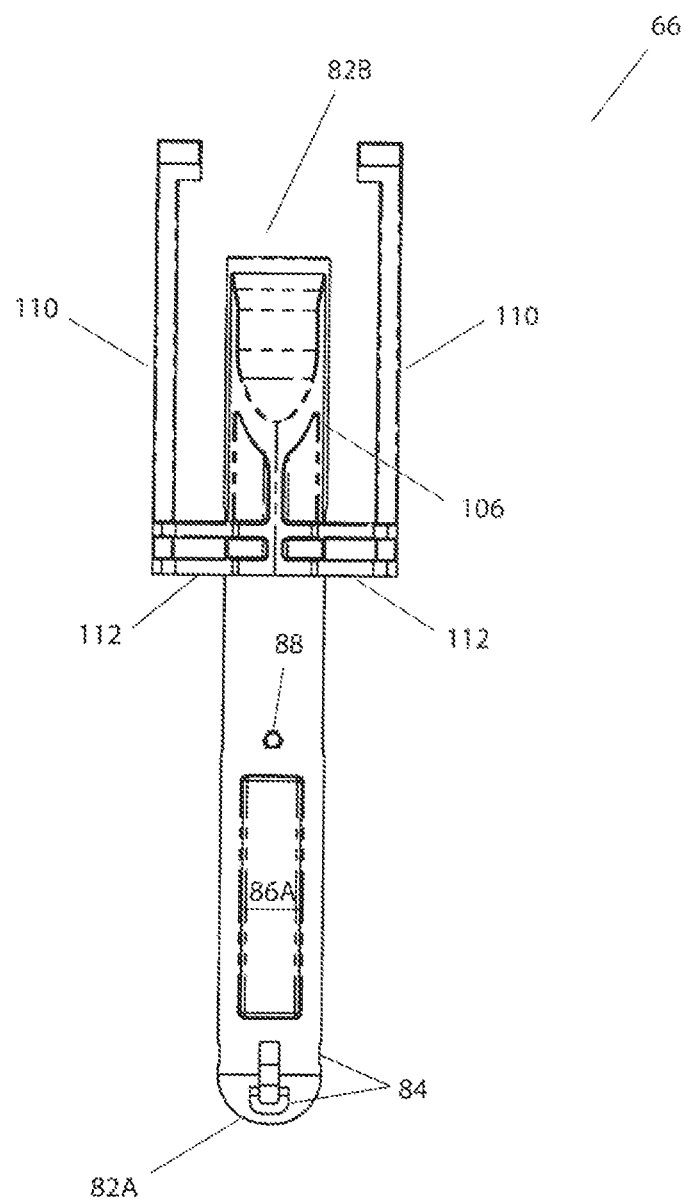
FIG. 19 is a bottom plan view of the plunger assembly.
Figure 23:
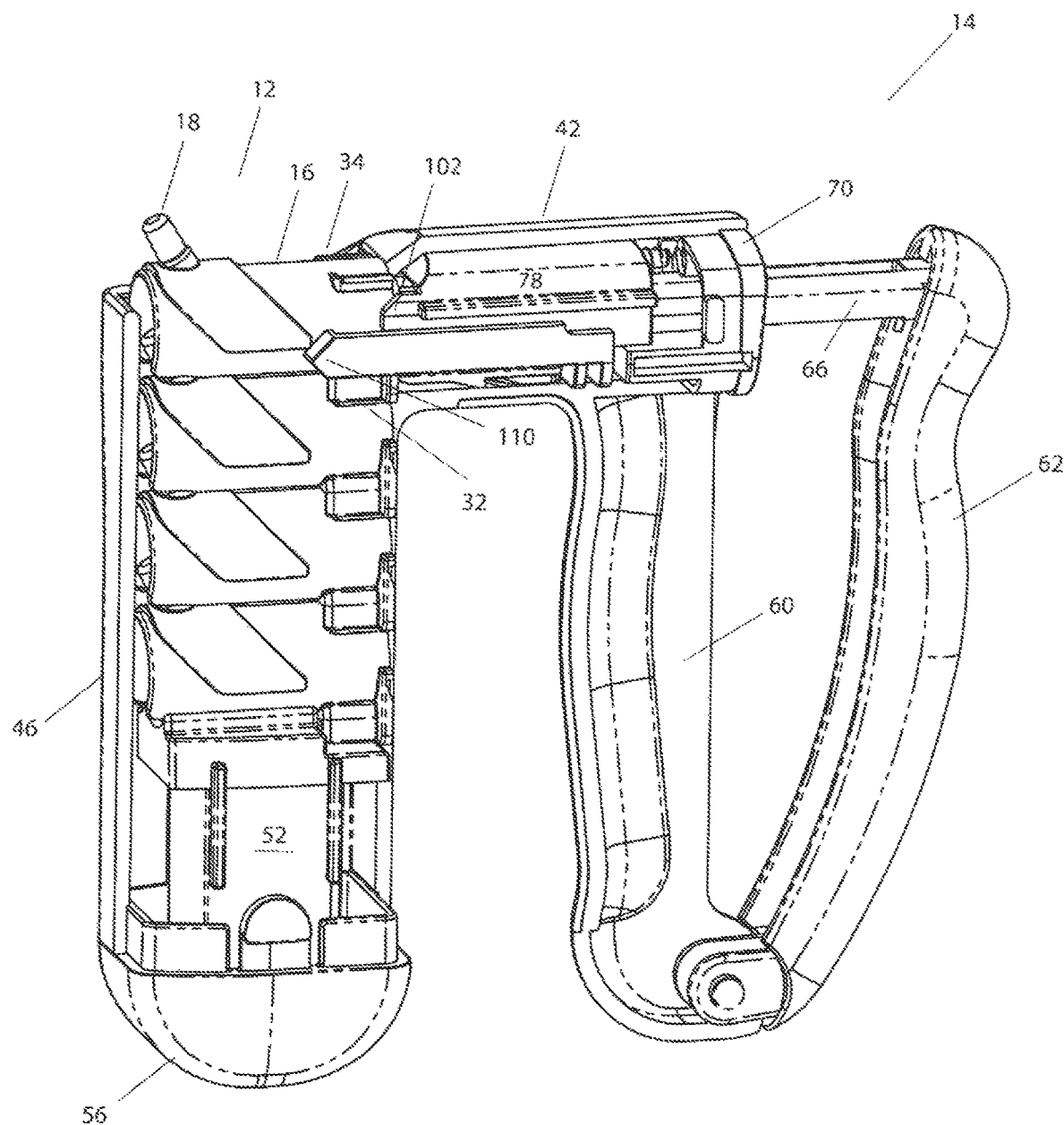
FIG. 23 is a perspective view of the dispenser gun of FIG. 22 in a second state, wherein the plunger is advanced to a point where it begins to push a cap off a top cartridge.

Referring to FIGS. 18, 21 and 23, the final feature of the plunger body 66 is a pair of leading arms 110 which extend past the distal forward end 828 and run parallel to the plunger 66. The leading arms 110 are connected to the plunger body 66 by short perpendicular arms 112. The leading arms 110 feature wide pointed tips extending inward toward the axis of the plunger body 66. The purpose of the leading arms 110 is to enable the plunger 66 to remove the cap 18 of the cartridge 12 in the breach 48. This task is accomplished as the knob 88 of the plunger body 66 reaches position 92B. The plunger body 66 must retract slightly as the knob 88 moves to position 92C, before continuing to advance, so that the cap 18 has time to clear the nozzle 26 before the product in the cartridge 12 begins to be expelled.

D. Actuation Sequence

Figure 24:
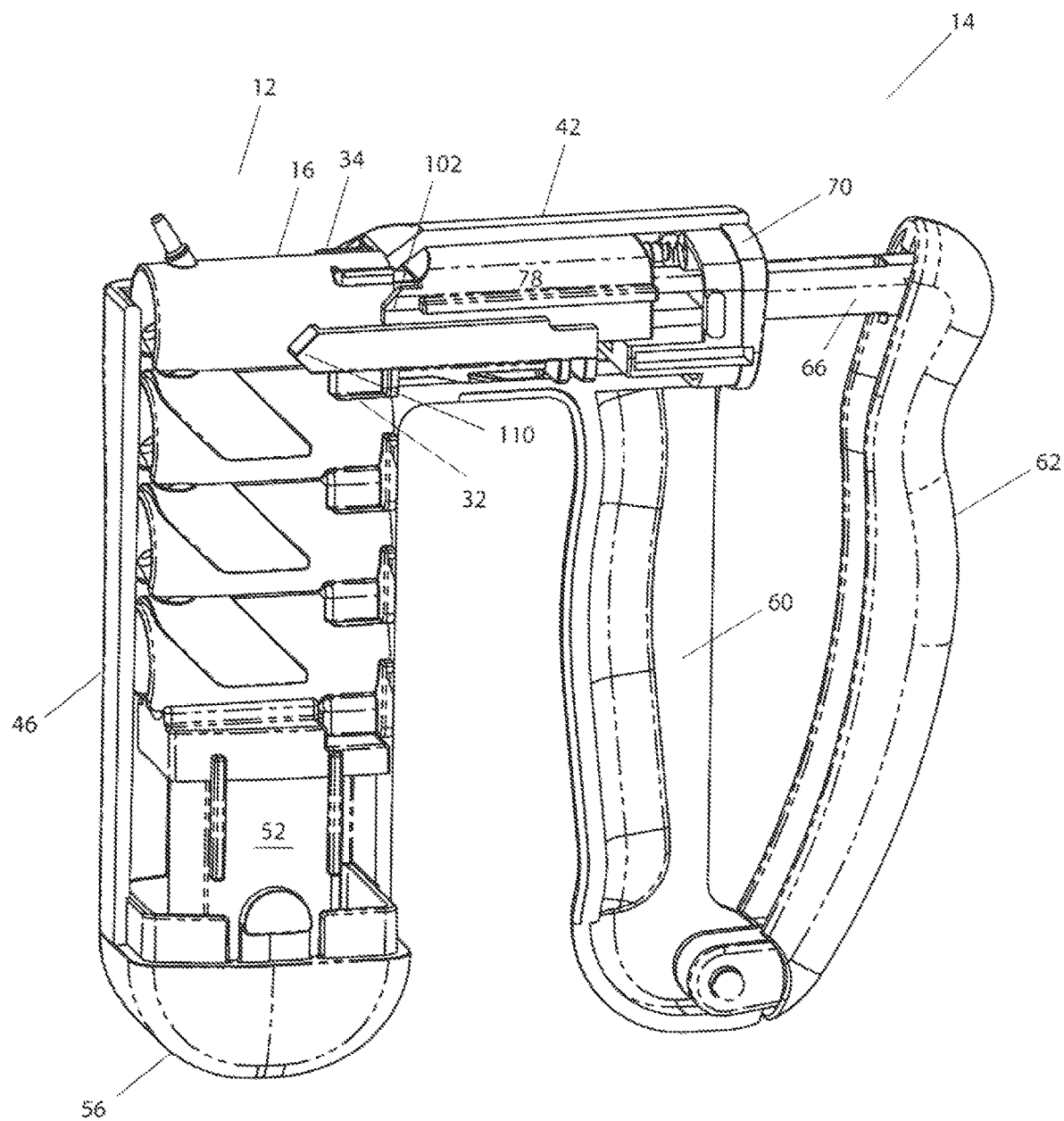
FIG. 24 is a perspective view of the dispenser gun of FIG. 22 in a third state, wherein the cap is completely removed from the cartridge, and the plunger is in position to deliver a dosage.
Figure 25:
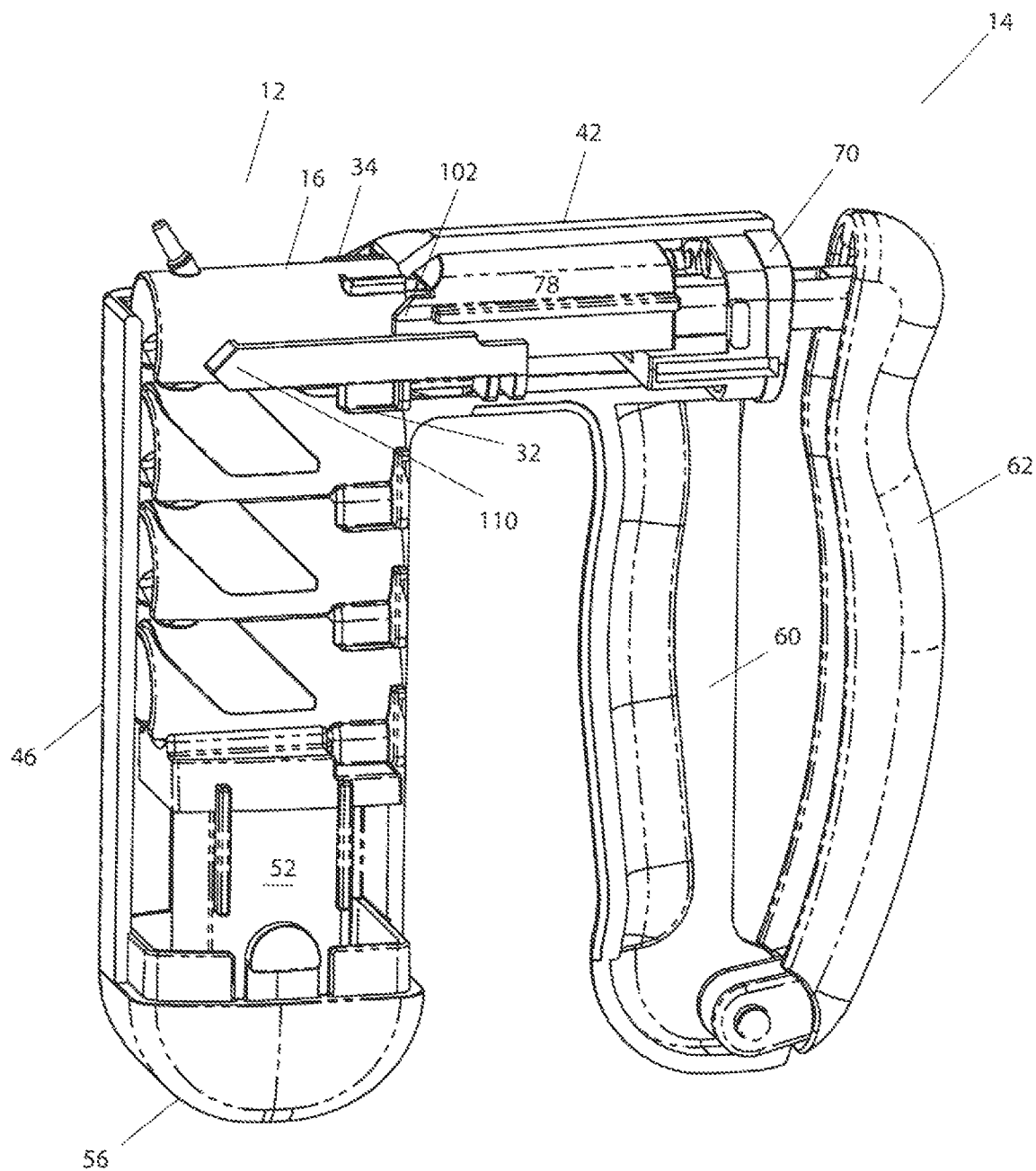
FIG. 25 is a perspective view of the dispenser of FIG. 22 in a fourth state, wherein the plunger is in a fully extended position, the gun having dispensed the entire dosage.

A representative actuation sequence is shown in FIGS. 22-25. In FIG. 22, the trigger 62 is fully withdrawn from the body 42 of the gun 14, ready to be advanced by a hand squeeze action. In FIG. 23, the trigger 62 is advanced approximately 3 mm and the leading arms 110 of the plunger body 66 make contact with the tips of the nozzle cap 18, forcing the cap 18 off of the nozzle 26. In FIG. 24, the dispenser gun 14 is now ready to dispense the product. The plunger 66 makes contact with and advances the piston 20 of the cartridge 12 forward, thereby forcing the product out of the nozzle 26. As the plunger 66 advances, the plunger barb 94 passes under the slide barb 100 and the wedge-shaped blade 106 enters the space between the top two cartridges 12, separating the top cartridge 12 to enable ejection. In FIG. 25, the plunger 66 has advanced the cartridge piston 20 to its limit, expelling all the product. As the plunger 66 begins to retract, the plunger barb 94 pulls the slide 78 back by the slide barb 100 allowing the top cartridge 12 to eject, and the magazine spring 54 to move the next cartridge 12 into the breach 48.

E. Dimensions and Materials

The body 42 is preferably constructed of a rigid, but lightweight polymeric material, more preferably nylon and most preferably nylon 6F20. In the preferred embodiment shown, the dimensions of the gun 14 are 5.7 in. (14.5 cm.)—height, 6.1 in. (15.5 cm.)—width and 1.4 in. (3.6 cm.)—thickness. The top and bottom surfaces and edges of the body 42 are preferably radiused for ease of manual handling by the user. The dimensions of the magazine are complementary with the dimensions of the stack of cartridges 12 which is contained therein. In the embodiment shown, the cartridges 12, when stacked together, have dimensions of 1.6 in. (4.15 cm.)—height, 3.5 in. (8.9 cm.)—width and 0.8 in. (2.1 cm.)—thickness. Accordingly, the magazine 18 has dimensions of 4.4 in. (11.2 cm.)—height, 1.65 in. (4.2 cm.)—width and 1.15 in. (2.1 cm.)—thickness to provide an internal cavity for housing the cartridges 12.

All the examples shown and described above are designed primarily for injecting material into teat canals. It is envisaged that with minor variations the cartridges 12 and apparatus could be used to inject products into other cavities.

In the examples described above, the dispenser gun 14 is designed to dispense four cartridges prior to reloading the magazine. It is envisaged that variations of the gun 14 could be adapted to dispense fewer or more cartridges 12 as desired.

In summary, it will be understood that some embodiments of the invention enable a dosing cartridge 12 and a dispenser gun combination which:
  facilitates reduction in the total volume of plastic packaging used to store the formulations, i.e. because one gun may have multiple cartridges 12, while still ensuring each dose is still in its own separate package.
  is simple to load, use and operate with a very comfortable ergonomic design, does not require the user to undertake secondary actions to remove the cap of each cartridge; this procedure is automatically accomplished at the same time as the user is delivering the dose of the cartridge preceding the dose from which the cap is being removed, and/or The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

What is claimed is:

1. A dosing apparatus, comprising:
   (a) the at least one cartridge for holding at least one product, at least one cartridge having a body defining a cavity for holding the at least one product, a nozzle disposed on the body and communicatively connected to the cavity for dispensing the at least one product from the cavity, and a piston arranged to move within the cavity to propel the at least one product from the cavity into the nozzle;
   (b) a cap removably coupled to the at least one cartridge for protecting the nozzle; and
   (c) a dispenser for holding the at least one cartridge, and adapted to remove the cap from the at least one cartridge and actuate the piston, whereby the at least one product is dispensed from the at least one cartridge wherein the dispenser comprises:
   a magazine for holding the at least one cartridge;
   an actuator communicatively connected to the magazine and aligned longitudinally with respect to the body of the at least one cartridge for actuating the piston, wherein the actuator includes the following sub-parts:
   a plunger having an end which advances the piston and wherein the end of the plunger is cylindrical;
   a pair of leading arms, connected to sides of the plunger, and extending out in front of and parallel to the plunger;
   a wedge shaped blade, connected to a bottom of a center of the plunger and disposed parallel to the plunger, with a tip of the blade facing the magazine;
   a barb, extending upwards from a top of the center of the plunger, and connected to the plunger by a flexible arm disposed parallel to the plunger;
   a slide, positioned on top of the cylindrical end of the plunger and in sliding contact with the plunger;
   a spring which is positioned between the slide and a back of the dispenser, being secured on a knob extending out a rear of the slide; and;
   a grooved block which is square shaped, the groove being in sliding contact with a cylindrical knob disposed on the bottom of the plunger.

2. The dosing apparatus of claim 1, wherein the cavity has a cylindrical geometry and is aligned longitudinally with respect to the body.

3. The dosing apparatus of claim 2, wherein the nozzle is communicatively connected to the cavity via a passage.

4. The dosing apparatus of claim 2, wherein the piston has a circular geometry and is sealingly movable in the cavity.

5. The dosing apparatus of claim 1, wherein the nozzle is disposed at a predetermined angle less than 90° relative to the body.

6. The dosing apparatus of claim 5, wherein the predetermined angle is approximately 60 degrees.

7. The dosing apparatus of claim 1, wherein the at least one cartridge is a plurality of cartridges arranged in a stack, each cartridge further has a means to removably connect to adjacent cartridges of the plurality of cartridges.

8. The dosing apparatus of claim 7, wherein the means to connect comprises a pair of hooks on a lower surface of the at least one cartridge, and a pair of complementary tabs on a upper surface of the at least one cartridge.

9. The dosing apparatus of claim 7, wherein the plunger advances the piston, the pair of leading arms remove the cap, the wedge shaped blade separates a topmost cartridge of the plurality of cartridges from the stack, the barb catches on the slide to retract the slide, the slide prevents the topmost cartridge held in the magazine from being ejected from the dispenser, the spring biases the slide to anon-retracted disposition, and the grooved block divides an actuation sequence into a first hand squeeze action for cap removal and a second hand squeeze action for expelling the at least one product.

10. The dosing apparatus of claim 9, wherein a trigger mechanism automatically withdraws after actuating one cartridge of the plurality of cartridges and the magazine loads a subsequent cartridge.

11. The dosing apparatus of claim 1, wherein the actuator is hand powered, and further comprises a handle, a trigger pivotally connected to the handle and to the actuator, and a trigger spring coupled to the handle and to the trigger.

12. The dosing apparatus of claim 1, wherein the plunger, the pair of arms, the edge shaped blade, and the barb are unitary.

13. The dosing apparatus of claim 1, wherein the apparatus is used to administer a prophylactic or therapeutic mastitis product to a teat of a dairy cow, the nozzle being adapted to engage the teat.

* * * * *